United States Patent [19]

Cummings et al.

[11] Patent Number: 5,670,191
[45] Date of Patent: Sep. 23, 1997

[54] ALIPHATIC AMIDE FEED SUPPLEMENT FOR RUMINANTS

[75] Inventors: Kenneth R. Cummings, Skillman; Ronald L. Forrest, Cranbury, both of N.J.

[73] Assignee: Church & Dwight Co., Inc., Princeton, N.J.

[21] Appl. No.: 534,066

[22] Filed: Sep. 26, 1995

[51] Int. Cl.[6] .................. C07C 231/00; A61K 31/95; A23K 1/00; A23D 7/005
[52] U.S. Cl. .................. 426/2; 426/601; 426/807; 426/630; 426/635; 426/636; 554/35; 514/558; 514/560
[58] Field of Search .................. 426/2, 601, 807, 426/630, 635, 636; 554/35; 514/558, 560

[56] References Cited

U.S. PATENT DOCUMENTS

| | | |
|---|---|---|
| 3,253,006 | 5/1966 | Davis . |
| 3,925,560 | 12/1975 | Scott ............................ 426/807 |
| 3,932,476 | 1/1976 | Bergeron . |
| 4,642,317 | 2/1987 | Palmquest et al. ............ 514/558 |
| 4,826,694 | 5/1989 | McAskie ........................ 426/74 |
| 4,853,233 | 8/1989 | McAskie ........................ 426/74 |
| 4,909,138 | 3/1990 | McAskie ........................ 99/536 |
| 5,143,737 | 9/1992 | Richardson ..................... 426/2 |
| 5,416,115 | 5/1995 | Erdman et al. ................ 514/560 |

*Primary Examiner*—Donald E. Czaja
*Assistant Examiner*—Choon P. Koh
*Attorney, Agent, or Firm*—Irving H. Fishman

[57] ABSTRACT

A feedstock and a method of utility are provided for increasing the content of unsaturated fatty acids in the tissues and milk of ruminants. A preferred feedstock is composed of a fodder substrate which is blended with an unsaturated aliphatic amide ingredient such as soyamide. The unsaturated aliphatic amide is biohydrogenation-resistant, and bypasses the rumen substantially intact. The aliphatic amide is converted to free fatty acid in the digestive tract, and subsequently is absorbed in the tissues and milk of the ruminant.

12 Claims, No Drawings

ALIPHATIC AMIDE FEED SUPPLEMENT FOR RUMINANTS

BACKGROUND OF THE INVENTION

Conventional cattle feeds such as corn and alfalfa often fail to provide sufficient energy for cattle, especially lactating dairy cattle during periods of heavy milk production. Feed containing a high proportion of corn also has a tendency to depress the milk fat content of the milk produced by such cattle. Fat is an excellent energy source, and it is known that if the proportion of fat in cattle food is increased, lactating dairy cattle produce high milk yields without draining their reserves of body fat and without diminishing the proportion of milk fat in the milk produced.

However, it has been found that if the proportion of fat in the diet of cattle exceeds about 5% of the total feed in solids, the feed has toxic effects upon the microorganisms in the rumen of the cattle. It appears that fat reduces the growth rate or even kills certain microorganisms which digest fiber in the cow's rumen, thereby lowering fiber digestibility. This deleterious effect on the cow's rumen is particularly true of unsaturated fats.

It is known also that triglycerides and free fatty acids can physically coat fibrous or cellulosic material in the rumen and inhibit fermentation of the material by the bacteria. This has an adverse effect on the total digestibility of the diet, and can result in a reduced yield of milk and milk fat.

There has been a continuing need for new dietary supplements for animal feedstuff which can be fed to ruminant animals without interfering with feed metabolism by rumen microorganisms, and which have a high level of digestibility.

U.S. Pat. Nos. 4,642,317; 4,826,694; 4,853,233; and 4,909,138 describe the incorporation of insoluble fatty acid salts in ruminant feed as a means of increasing the fat content of the feed without deleteriously affecting the ruminant digestion cycle. A feed additive such as fatty acid calcium salt functions as a rumen bypass product, and is subsequently metabolized in the abomasum or small intestine of the ruminant.

U.S. Pat. No. 5,416,115 describes a method of regulating milk fat and milk production using an insoluble form of trans-fatty acid derivative.

A more recent consideration has been the types of fatty acids which are nutritive elements in the animal food chain. Saturated fatty acids are known to cause adverse health effects, such as coronary heart disease and high blood pressure in humans. It is also known that olefinically unsaturated fatty acids such as oleic acid and linoleic acid are nutritionally more favorable for human diet.

Ruminants such as cattle are the main source of red meat and dairy products for human consumption. It has been determined that unsaturated fatty acids are susceptible to biohydrogenation by microorganisms in the rumen of ruminants. The higher content of saturated fatty acids is absorbed in the digestive tract and there is an increase in the amount of saturated fatty acids in the tissues and milk of the ruminants.

Recent investigations have been directed to methods for inhibiting biohydrogenation of unsaturated fatty acids in the rumen. It has been postulated that ruminal bacteria biohydrogenate unsaturated fatty acids which have a free carboxylic acid group. Based on this premise, attention has been directed to unsaturated fatty acid analogs which did not have a free carboxylic acid group.

An in vitro procedure has been conducted to determine the ability of N-linoleic acid amide methionine ester to resist hydrolysis and biohydrogenation by ruminal microorganisms. It was found that the linoleic acid amide derivative exhibited resistance to hydrolysis and biohydrogenation by the ruminal bacteria. The study is reported in the Journal of Dairy Science, 75 1527 (1992).

Another important factor in the preparation of ruminant feedstocks with a content of fatty acid supplement is the level of digestibility of the fatty acid ingredient. Fatty acids and fatty acid salts and analogs differ in the proportion of fatty acid which is digested and absorbed, relative to the unabsorbed fatty acid which passes out of the digestive tract as solid waste.

There is continuing interest in the development of new methods and feedstocks for increasing the content of unsaturated fatty acids in the tissues and milk of ruminants.

Accordingly, it is an object of this invention to provide a method for producing meat and dairy products from ruminants that are healthier for human consumption.

It is another object of the invention to provide a process for the production of a ruminant feed supplement which can function as a rumen bypass composition, and permit a beneficial increase in the dietary fat content of the feed.

It is another object of this invention to provide a feed supplement comprising unsaturated fatty acids that are protected from biohydrogenation in the rumen of ruminants.

It is another object of this invention to provide a feed supplement for ruminants that will increase the amount of unsaturated fatty acids absorbed into the blood stream of the animal.

It is another object of this invention to provide a feed supplement for ruminants which comprises an unsaturated fatty acid analog which is absorbed with minimal loss as undigested feed.

It is a further object of this invention to provide a naturally-derived cattle milk product with a milk fat which has an elevated oleic acid content.

Other objects and advantages of the present invention shall become apparent from the accompanying description and examples.

DESCRIPTION OF THE INVENTION

One or more objects of the present invention are accomplished by the provision of a method for increasing the amount of unsaturated fatty acids in the tissues and milk of ruminants which comprises feeding a ruminant with a feedstock containing an unsaturated aliphatic amide supplement ingredient which is resistant to biohydrogenation in the rumen, wherein the aliphatic amide corresponds to the formula:

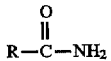

where R is an unsaturated $C_{11}$–$C_{21}$ aliphatic substituent.

The acyl moiety (RCO—) in the above formula is derived from unsaturated fatty acids such as dodecylenic acid, palmitoleic acid, oleic acid, vaccenic acid, linoleic acid, linolenic acid, gadoleic acid, cetoleic acid, and the like.

The invention unsaturated aliphatic amide can be synthesized from naturally occurring fatty ester mixtures, such as the fatty acid glyceride mixtures characteristic of palm oil, cottonseed oil, soybean oil, rapeseed oil, tallow, and the like, or the free fatty acids derived therefrom.

Palm fatty acid distillate (PFAD) has the following weight percent content of fatty acids:

| Palmitic acid | 38–50 |
|---|---|
| Oleic acid | 35–40 |
| Linoleic acid | 5–10 |
| Stearic acid | 3–6 |
| Lauric acid | 1–3 |

A commercially available beef tallow fatty acid mixture has the following weight percent of free fatty acids:

| Palmitic acid | 22–28 |
|---|---|
| Oleic acid | 38–44 |
| Linoleic acid | 3–6 |
| Stearic acid | 18–24 |

The fatty acid triglyceride constituency of the oil component of a whole oilseed is different for the various oilseed sources.

Soybean has a weight percent fatty acid profile comprising lauric (0.5), myristic (0.5), palmitic (12), stearic (4), oleic (25), linoleic (52), and linolenic (6).

Cottonseed has a weight percent fatty acid profile comprising myristic (0.7), palmitic (24), stearic (2), palmitoleic (1), oleic (17), linoleic (55), and linolenic (0.3).

Rapeseed has a weight percent fatty acid profile comprising palmitic (5), stearic (2), oleic (63), linoleic (20), linolenic (9), and eicosenic (1).

The following equations illustrate the synthesis of unsaturated aliphatic amides:

(1) $R-CO_2H+NH_3 \rightarrow R-CO-NH_2+H_2O$ (2) 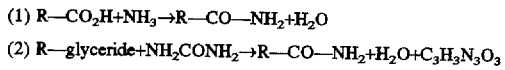

Processes for production of aliphatic amides are described in publications such as U.S. Pat. Nos. 915,680; 2,109,941; 2,608,562; 3,244,734; 3,253,006; 3,932,476; and 4,655,972; incorporated by reference.

One preferred type of unsaturated aliphatic amide is synthesized by the reaction of soybean oil with ammonia. Whole soybeans also can be employed to provide protein as an additional nutrient.

A present invention aliphatic amide feed supplement can be admixed with a conventional fodder for facilitating ingestion by ruminants. The aliphatic amide feed supplement is incorporated in a fodder in an amount which is effective for increasing absorption and deposition of unsaturated fatty acids in the tissues and milk of a ruminant. Typically the aliphatic amide content in a base feed for ruminants will be in the range between about 0.5–20 weight percent, preferably between about 3–8 weight percent. A base feed normally is selected from corn, hay, grass, barley, oats, sorghum, wheat, bran, hominy, and mixtures thereof.

An aliphatic amide supplement can comprise a mixture of unsaturated and saturated fatty acid amides. When an aliphatic amide ruminant feed supplement is a mixture of fatty acid amides, preferably the supplement contains at least about 40 weight percent of oleic acid amide or linoleic acid amide or a mixture thereof, and most preferably contains at least about 70 weight percent of this type of unsaturated fatty acid amide.

One or more other ingredients can be incorporated in a present invention feedstock composition, such as biologically active derivatives.

An optional biologically active ingredient can be included in a feedstock in an effective quantity between about 0.05–20 weight percent, based on the weight of feedstock. It can be selected from a broad variety of nutrients and medicaments, either as a single component or as a mixture of components, which are illustrated by the following listing of active molecular species:

1. $C_2-C_{22}$ aliphatic carboxylic acids and alkali metal, ammonium and alkaline earth metal salts which can be different or have some correspondence with the other fatty acid constituents present in the aliphatic amide ingredient.

2. sugars and complex carbohydrates which include both water-soluble and water-insoluble monosaccharides, disaccharides and polysaccharides.

Cane molasses is a byproduct from the extraction of sucrose from sugar cane. It is commercially available at standard 79.5° Brix concentration, which has a water content of about 21 weight percent, and a sugar content of 50 weight percent. Sugar beet byproducts also are available as low cost carbohydrate sources.

Whey is a byproduct of the dairy industry. The whey is a dilute solution of lactalbumin, lactose, fats, and the soluble inorganics from milk. Dried whey solids typically have the following composition.

| Protein | 12.0% |
|---|---|
| Fat | 0.7% |
| Lactose | 60.0% |
| Phosphorus | 0.79% |
| Calcium | 0.874 |
| Ash | 9.7% |

Another source of carbohydrate is derived from the pulp and paper industry which produces large quantities of byproduct lignin sulfonates from wood during the sulfite pulping process. The carbohydrate byproduct is a constituent of the spent sulfite liquor.

3. aminoacid ingredients either singly or in combination which include arginine, histidine, isoleucine, leucine, lysine, methionine, phenylalanine, threonine, tryptophan, valine, tyrosine ethyl HCl, alanine, aspartic acid, sodium glutamate, glycine, proline, serine, cysteine ethyl HCl, and the like, and analogs and salts thereof.

4. vitamin ingredients either singly or in combination which include thiamine HCl, riboflavin, pyridoxine HCl, niacin, niacinamide, inositol, choline chloride, calcium pantothenate, biotin, folio acid, ascorbic acid, vitamin $B_{12}$, p-aminobenzoic acid, vitamin A acetate, vitamin K, vitamin D, vitamin E, and the like.

Trace element ingredients include compounds of cobalt, copper, manganese, iron, zinc, tin, nickel, chromium, molybdenum, iodine, chlorine, silicon, vanadium, selenium, calcium, magnesium, sodium and potassium.

5. protein ingredients as obtained from sources such as dried blood or meat meal, dried and sterilized animal and poultry manure, fish meal, liquid or powdered egg, fish solubles, cell cream, soybean meal, cottonseed meal, canola meal, and the like.

Protein equivalent ingredients include non-protein nitrogen compounds such as urea, biuret, ammonium phosphate, and the like.

6. medicament ingredients either singly or in combination which include promazine hydrochloride, chloromadionate acetate, chlortetracycline, sulfamethazine, monensin, poloxaline, and the like. Oxytetracycline is a preferred antibiotic for cattle prophylaxis.

7. antioxidants as illustrated by butylated hydroxyanisole, butylated hydroxytoluene, tocopherol, tertiary-butylhydroquinone, propyl gallate, and ethoxyquin; and suitable preservatives include sodium sorbate, potassium sorbate, sodium benzoate, propionic acid, α-hydroxybutyric acid, and the like.

8. suspension stabilizing agents which preferably are selected from nonionic surfactants, hydrocolloids and cellulose ethers. These types of chemical agents are illustrated by polyethylene oxide condensates of phenols, $C_8$–$C_{22}$ alcohols and amines; ethylene oxide reaction products with fatty acid partial esters of hexitans; alkylarylpolyoxyethylene glycol phosphate esters; gum arabic; carob bean gum; tragacanth gum; ammonium, sodium, potassium and calcium alginates; glycol alginates; xanthan gum; potato agar; alkylcellulose; hydroxyalkylcellulose; carboxyalkylcellulose; and the like.

Ruminants are a class of even-toed hoofed mammals that chew the cud and have a complex three or four chambered stomach, such as cattle, sheep, goats and deer. Because of the multiple stomach functionality, the digestive system of ruminants differs substantially from that of monogastric animals.

The first and largest stomach located after the esophagus in ruminants is referred to as the rumen. Unique to ruminants, the rumen contains microorganisms, such as bacteria and protozoa, which break down complex compounds ingested by the animal by a process known as ruminal fermentation. Among the substances and compounds transformed by these microorganisms are unsaturated fatty acids. When a ruminant ingests an unsaturated fatty acid such as oleic acid, at least a portion of the unsaturated fatty acid is converted to a saturated fatty acid which is absorbed in the tissues and milk of the animal.

An essential aspect of the present invention is the feeding of ruminants with a feed containing an unsaturated aliphatic amide feed supplement which exhibits rumen-bypass properties, and which is capable of resisting ruminal degradation. A present invention unsaturated aliphatic amide bypasses the rumen substantially intact, and is absorbed as free fatty acid from the digestive tract, and subsequently is transferred into the tissues and milk of ruminants.

The unsaturated aliphatic amide feed supplement in accordance with the present invention does not cause harmful side effects in a ruminant. Normally, when free fatty acids are increased in the diet of a ruminant, the fatty acids have an inhibitory effect on bacterial fermentation within the rumen. However, a present invention unsaturated aliphatic amide does not demonstrate a similar effect.

A present invention unsaturated aliphatic amide ruminant feed supplement is a convenient and economical means for increasing the amount of unsaturated fatty acids absorbed and deposited in the tissues and milk of ruminants such as Holstein and Jersey dairy cattle. It is a unique aspect of the present invention that the unsaturated aliphatic amide does not have toxic effects on the microorganisms in the rumen.

The present invention further contemplates the application of a present invention unsaturated aliphatic amide feed supplement to a herd of dairy cattle in a controlled feeding regimen, whereby the average naturally-derived milk product from the herd has a milk fat content which contains between about 35–42 weight percent of oleic acid, based on the milk fat weight.

A present invention unsaturated aliphatic amide, which is a N-unsubstituted compound, has significant advantages as a ruminant feed supplement, in comparison to an unsaturated aliphatic amide compound which is N-monosubstituted or N-disubstituted as illustrated by the following structure:

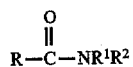

where at least one of $R^1$ or $R^2$ is an organic substituent such as an alkyl radical.

An unsaturated and N-unsubstituted aliphatic amide feed supplement in accordance with the present invention is palatable and has good acceptance by feeding ruminant. A present invention aliphatic amide exhibits a high level of biohydrogenation-resistance in the rumen, and does not interfere with ruminal fermentation.

Further, a present invention N-unsubstituted aliphatic amide is more readily absorbed in the digestive tract of a ruminant than a corresponding N-substituted aliphatic amide, as there is less loss as undigested solid waste matter.

The following examples are further illustrative of the present invention. The components and specific ingredients are presented as being typical, and various modifications can be derived in view of the foregoing disclosure within the scope of the invention.

EXAMPLE I

This Example illustrates the beneficial effects derived by feeding an unsaturated aliphatic amide feed supplement to ruminants in accordance with the present invention.

The relative ruminal biohydrogenation-resistance and digestibility of a present invention soyamide in comparison to soybean oil and butylsoyamide are demonstrated in accordance with the procedures described in J. Anim. Sci., 73, 818 (1995) by T. C. Jenkins.

Twelve Hampshire x Suffolk wethers, averaging 34±3.2 kg initial BW, are shorn and dewormed, then randomly assigned to four diets. One diet contains no added fat, whereas the other three diets contain 5% added fat (DM basis) as either soybean oil, butylsoyamide or soyamide. Total diets consist of corn silage and concentrate (1:1, DM basis) mixed daily. Silage contains 25.5% DM, 6.4% CP, and 37.3% ADF on a DM basis. Feed DM offered to each wether is restricted throughout the study to 3% of its initial BW to eliminate intake effects on digestibility. Feed is given twice daily in equal amounts at 0900 and 1900.

Corn in the control concentrate is substituted with soybean oil, butylsoyamide or soyamide plus additional soybean meal to keep diets isonitrogenous. Diets are formulated to meet or exceed minimum nutritional requirements of sheep according to NRC (1985).

Blood and ruminal samples, and digestibility measurements and amide analyses, are managed with the methods described in the J. Anim., Sci., 73, 818 (1995) publication.

Relative to the control diet, soybean oil increases plasma linoleic acid concentration 22%, the butylsoyamide increases linoleic acid by 58%, and the soyamide increases linoleic acid by 61%. The increase in plasma unsaturated fatty acids demonstrates at least partial resistance of the fatty acid amides to ruminal biohydrogenation, and their digestion and absorption postruminally.

For the butylsoyamide diet, amide intake averages 47 g/d, and excretion of amide averages about 29 g/d, which corresponds to an apparent digestibility coefficient for butylsoyamide of about 38%.

For the soyamide diet, amide intake averages 49 g/d, and excretion of amide averages about 21 g/d, which corresponds to an apparent digestibility coefficient for soyamide of about 57%.

Fatty acid digestibilities for the Control and soybean oil diets are about 81% and 86% respectively.

The digestibility coefficients indicate that butylsoyamide and soyamide have lower digestibility than soybean oil, and soyamide has a higher digestibility than butylsoyamide.

The comparative data indicate that soyamide and butylsoyamide are more resistant to ruminal biohydrogenation than soybean oil, and soyamide is more resistant to ruminal biohydrogenation than butylsoyamide.

The comparative data also indicate that soyamide is more digestible than butylsoyamide.

EXAMPLE II

This Example illustrates the beneficial increase in oleic acid content in cattle milk when an unsaturated aliphatic amide is included in dairy feedstock in accordance with the present invention.

Six lactating Jersey cows (mean BW 430 kg) are housed in a tie-stall barn and fed ad libitum twice daily (0800 and 1700) a diet of concentrate mix, corn silage (40% dry matter) and chopped alfalfa hay in a ratio of 1:1:1. The cows are in a 6×6 Latin square to compare the effects of the fatty acid feed supplements.

The fatty acid feed supplement is in the form of a calcium salt of palm fatty acid distillate (Megalac, Church & Dwight Co.), or soyamide.

Table 1 illustrates the composition of the basal concentrate mix. Table 2 lists the nominal unsaturated fatty acid content of Megalac and soyamide, respectively. Table 3 illustrates the effect of the fatty acid feed supplement type on the unsaturated fatty acid content of the dairy milk.

The comparative data indicate that soyamide is effective for providing cattle milk with an oleic acid content in the range between about 35–42 weight percent, based on the milk fat weight.

TABLE 1

| Basal Concentrate Mix | |
|---|---|
| Ingredient | Weight % |
| Ground ear corn | 47.74 |
| Oats | 12.17 |
| Soybean meal | 22.00 |
| Dehy alfalfa | 4.00 |
| Brewers grains | 4.00 |
| Linseed meal | 4.00 |
| Molasses, dried | 2.00 |
| Urea | .35 |
| Dicalcium phosphate | 2.21 |
| Vitamins and minerals | 1.53 |
| Nitrogen, % | 3.35 |
| Fatty acids, % | 3.88 |

TABLE 2

| Fatty Acid Content Of Feed Supplement | | |
|---|---|---|
| | Weight % | |
| Feed Supplement | Oleic Acid | Linoleic Acid |
| Megalac Ca salt | 34 | 8 |
| Soyamide | 25 | 52 |

TABLE 3

| Feed Supplement Effect On Milk Fat Composition | | |
|---|---|---|
| Feed Supplement | Oleic Acid | Linoleic Acid |
| Megalac Ca salt | 26 | 3 |
| Soyamide | 39 | 28 |

What is claimed is:

1. A method for increasing the amount of unsaturated fatty acids in the tissues and milk of ruminants which comprises feeding a ruminant with a feedstock containing an unsaturated aliphatic amide supplement ingredient which is resistant to biohydrogenation in the rumen, wherein the aliphatic amide corresponds to the formula:

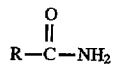

where R is an unsaturated $C_{11}$–$C_{21}$ aliphatic substituent.

2. A method in accordance with claim 1 wherein the ruminants are cattle or sheep.

3. A method in accordance with claim 1 wherein the feedstock comprises a mixture of a fodder and between about 0.5–20 weight percent of aliphatic amide ingredient.

4. A method in accordance with claim 1 wherein the aliphatic amide supplement is a mixture of fatty acid amides having a content of at least about 40 weight percent of unsaturated fatty acid amide.

5. A method in accordance with claim 1 wherein the aliphatic amide supplement is a mixture of fatty acid amides having a content of at least about 70 weight percent of oleic acid or linoleic acid or a mixture thereof.

6. A feedstock for ruminants for increasing the unsaturated fatty acid content in the tissues and milk of the ruminants, which comprises a fodder substrate containing between about 2–20 weight percent of an aliphatic amide supplement which comprises an ingredient corresponding to the formula:

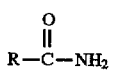

where R is an unsaturated $C_{11}$–$C_{21}$ aliphatic substituent.

7. A feedstock in accordance with claim 6 wherein the fodder substrate is selected from the group consisting of corn, hay, grass, barley, oats, sorghum, wheat, bran and hominy.

8. A feedstock in accordance with claim 6 wherein the aliphatic amide supplement is a mixture of fatty acid amides having a content of at least about 40 weight percent of unsaturated fatty acid amide.

9. A feedstock in accordance with claim 6 wherein the aliphatic amide supplement is a mixture of fatty acid amides having a content of at least about 70 weight percent of oleic acid or linoleic acid or a mixture thereof.

10. A feedstock in accordance with claim 6 which additionally contains an effective quantity between about 0.05–20 weight percent of a biologically active ingredient, based on the weight of feedstock.

11. A feedstock in accordance with claim 10 wherein the biologically active ingredient is a protein.

12. A feedstock in accordance with claim 10 wherein the biologically active ingredient is selected from the group consisting of aminoacids and analogs and salts thereof.

* * * * *